United States Patent
Connaughton et al.

(10) Patent No.: US 12,038,363 B2
(45) Date of Patent: Jul. 16, 2024

(54) BOB AND SHAFT DESIGNS FOR PORTABLE RHEOMETRY UNITS

(71) Applicant: Schlumberger Technology Corporation, Sugar Land, TX (US)

(72) Inventors: Jerry Connaughton, Houston, TX (US); Zakhar Chizhov, Katy, TX (US); Colin Stewart, Houston, TX (US)

(73) Assignee: Schlumberger Technology Corporation, Sugar Land, TX (US)

( * ) Notice: Subject to any disclaimer, the term of this patent is extended or adjusted under 35 U.S.C. 154(b) by 251 days.

(21) Appl. No.: 17/621,937

(22) PCT Filed: Jun. 30, 2020

(86) PCT No.: PCT/US2020/040257
§ 371 (c)(1),
(2) Date: Dec. 22, 2021

(87) PCT Pub. No.: WO2021/003134
PCT Pub. Date: Jan. 7, 2021

(65) Prior Publication Data
US 2022/0276145 A1 Sep. 1, 2022

Related U.S. Application Data

(60) Provisional application No. 62/869,001, filed on Jun. 30, 2019.

(51) Int. Cl.
*G01N 11/14* (2006.01)
*E21B 21/01* (2006.01)
*G01N 33/28* (2006.01)

(52) U.S. Cl.
CPC ........ *G01N 11/14* (2013.01); *G01N 33/2823* (2013.01); *E21B 21/01* (2013.01)

(58) Field of Classification Search
CPC ... G01N 11/14; G01N 11/142; G01N 33/2823
See application file for complete search history.

(56) References Cited

U.S. PATENT DOCUMENTS 4,299,118 A   11/1981   Gau et al.
4,484,468 A   11/1984   Gau et al.
(Continued)

OTHER PUBLICATIONS

Standard Guide for Selection of Tests for Traffic Paints, ASTM Standard D2205, 2020, 6 pages.
(Continued)

*Primary Examiner* — Kristina M Deherrera
*Assistant Examiner* — Jean F Morello
(74) *Attorney, Agent, or Firm* — Jeffrey D. Frantz (57) ABSTRACT

A bob for a viscometer in a portable rheology unit is provided. The bob may include a bob portion having a cylindrical portion and a first end portion, the cylindrical portion defining a first end of the bob. The bob may also include a plastic portion interfacing with an interior surface of the first end portion, wherein the plastic portion includes a conical area extending from a conical area first end to a conical area second end, and the conical second end is connected to an interior surface of the cylindrical portion. The bob may also include a sleeve portion connected to the plastic portion and a bob second end portion connected to the sleeve portion.

18 Claims, 5 Drawing Sheets

(56) References Cited

U.S. PATENT DOCUMENTS

| | | | |
|---|---|---|---|
| 4,557,142 A * | 12/1985 | Hensley | ............... E21B 49/005 73/54.32 |
| 6,571,609 B1 | 6/2003 | Bi | |
| 2010/0004890 A1 | 1/2010 | Tonmukayakul et al. | |
| 2011/0198187 A1 | 8/2011 | Lukay et al. | |

OTHER PUBLICATIONS

Standard Test Method for Thermal Endurance of Rigid Electrical Insulating Materials, ASTM Standard D2304, 2018, 7 pages.

Specification for Low-Alloy Steel Electrodes for Shielded Metal Arc Welding, American National Standard AWS A5.5/A5.5M:2014, 10th Edition, American Welding Society, 2014, 10 pages.

International Preliminary Report on Patentability issued in International Patent application PCT/US2020/040257, dated Jan. 13, 2022, 10 pages.

Standard Specification for Carbon and Alloy Steel Bars Subject to End-Quench Hardenability Requirements, ASTM Standard A304-16, 2016, 48 pages.

* cited by examiner

BOB AND SHAFT DESIGNS FOR PORTABLE RHEOMETRY UNITS

CROSS-REFERENCE TO RELATED APPLICATIONS

This application is a national stage entry under 35 U.S.C. 371 of International Application No. PCT/US2020/040257, filed Jun. 30, 2020, and claims priority to and the benefit of U.S. Provisional Patent Application No. 62/869,001, filed Jun. 30, 2019, which is incorporated by reference herein.

BACKGROUND

Rheology is the science and study of deformation of fluids and the flow of matter. Rheology is important in several fields of science and has several different uses in the industry including use in the extraction of hydrocarbons from reserves located in geological stratum. In the drilling of wellbores to extract hydrocarbons, water is mixed with different additives and pumped down a string of pipe, commonly referred to as a drill string. The water with the different additives ("mud") has several purposes. The mud is used to lift materials ("cuttings") generated by the rotary action of a drill bit. The cuttings are flushed to the top of the wellbore created through the action of the drill bit. The cuttings are then removed, and the mud may be reconditioned and recirculated to the down hole environment to lift further cuttings as the wellbore progresses into the geological stratum. As the additives may be expensive in production of the mud, it is generally desired to reuse the mud to achieve the best possible economics of wellbore formation.

The consistency of the mud used to lift the cuttings is important to the overall efficiency of the drilling process. Mud rheology is measured on a continual basis during the drilling process, and the rheology may be altered during the drilling process with additives or dilution to meet the needs of the operator. As an example, in water-based fluids, water quality and quantity may play an important role in how additives perform. In other embodiments, diesel and synthetic based fluids may be used. Further consideration must also be taken into account for temperature, temperature variations, and pressure.

Mud is tested by highly accurate rheology units and/or viscometers. These measurement units are precise pieces of equipment that may measure small differences in fluid properties for different fluid samples by using viscometers that have high precision bearings bob assemblies, a component of a viscometer, are removed from the viscometer prior to shipment to a wellsite due to the fragile nature of the bearings used or support of the bob assembly. The removal of components from the viscometer and subsequent reassembly at the well site takes time and involves precise assembly to ensure the resulting unit works properly.

There is a need to provide for a viscometer that does not require disassembly during shipping from a manufacturer to the wellsite.

There is a further need to provide a viscometer that has an increased life span compared to conventional apparatus.

There is a still further need to reduce costly shipping of viscometers to and from certified repair centers.

SUMMARY

So that the manner in which the above recited features of the present disclosure can be understood in detail, a more particular description of the disclosure, briefly summarized below, may be had by reference to embodiments, some of which are illustrated in the drawings. It is to be noted that the drawings illustrate only typical embodiments of this disclosure and are therefore not to be considered limiting of its scope, for the disclosure may admit to other equally effective embodiments without specific recitation. Accordingly, the following summary provides just a few aspects of the description and should not be used to limit the described embodiments to a single concept.

In one embodiment, a bob for a viscometer in a portable rheology unit is disclosed. The bob may comprise a bob portion having a cylindrical portion and a first end portion, the cylindrical portion defining a first end of the bob. The bob may further comprise a plastic portion interfacing with an interior surface of the first end portion, wherein the plastic portion comprises a conical area extending from a conical area first end to a conical area second end, and the conical second end is connected to an interior surface of the cylindrical portion. The bob may further comprise a sleeve portion connected to the plastic portion. The bob may further comprise a bob second end portion connected to the sleeve portion.

In another embodiment, a viscometer is disclosed. A viscometer may comprise a motor, and a switch operatively connected to the motor, wherein the switch is configured to connect the motor to an electrical source. The viscometer may also comprise a cup configured to hold a drilling fluid and a bob defining a hollow interior, and the bob further configured to be at least partially submerged in the fluid. The viscometer may also comprise a driving mechanism connected to the bob and the motor, wherein the driving mechanism conveys rotational movement from the motor to the bob to rotate the bob and a strain gauge configured to measure a torsion resistance of fluid interacting on an exterior portion of the bob. The viscometer may also comprise a platform configured to support the cup, wherein the platform is configured to move from a first position wherein the bob is outside of an interior of the cup to a second position wherein the bob is located within the interior of the cup.

In another example embodiment, a method of performing a viscosity test is disclosed. The method may comprise pouring a drilling fluid into a cup of a viscometer and immersing a hollow bob with an attached hollow sleeve into the drilling fluid within the cup. The method may further comprise rotating the hollow bob in the drilling fluid with a motor and reading a viscous drag of the drilling fluid on the hollow bob by a torsion measuring apparatus.

BRIEF DESCRIPTION OF THE DRAWINGS

So that the manner in which the above recited features of the present disclosure can be understood in detail, a more particular description of the disclosure, briefly summarized above, may be had by reference to embodiments, some of which are illustrated in the drawings. It is to be noted, however, that the appended drawings illustrate only typical embodiments of this disclosure and are therefore not be considered limiting of its scope, for the disclosure may admit to other equally effective embodiments.

To facilitate understanding, identical reference numerals have been used, where possible, to designate identical elements that are common to the figures ("FIGS"). It is contemplated that elements disclosed in one embodiment may be beneficially utilized on other embodiments without specific recitation.

DETAILED DESCRIPTION

In the following, reference is made to embodiments of the disclosure. It should be understood, however, that the disclosure is not limited to specific described embodiments. Instead, any combination of the following features and elements, whether related to different embodiments or not, is contemplated to implement and practice the disclosure. Furthermore, although embodiments of the disclosure may achieve advantages over other possible solutions and/or over the prior art, whether or not a particular advantage is achieved by a given embodiment is not limiting of the disclosure. Thus, the following aspects, features, embodiments and advantages are merely illustrative and are not considered elements or limitations of the claims except where explicitly recited in a claim. Likewise, reference to "the disclosure" shall not be construed as a generalization of inventive subject matter disclosed herein and shall not be considered to be an element or limitation of the claims except where explicitly recited in a claim.

Although the terms first, second, third, etc., may be used herein to describe various elements, components, regions, layers and/or sections, these elements, components, regions, layers and/or sections should not be limited by these terms. These terms may be only used to distinguish one element, components, region, layer or section from another region, layer or section. Terms such as "first", "second" and other numerical terms, when used herein, do not imply a sequence or order unless clearly indicated by the context. Thus, a first element, component, region, layer or section discussed herein could be termed a second element, component, region, layer or section without departing from the teachings of the example embodiments.

When an element or layer is referred to as being "on," "engaged to," "connected to," or "coupled to" another element or layer, it may be directly on, engaged, connected, coupled to the other element or layer, or interleaving elements or layers may be present. In contrast, when an element is referred to as being "directly on," "directly engaged to," "directly connected to," or "directly coupled to" another element or layer, there may be no interleaving elements or layers present. Other words used to describe the relationship between elements should be interpreted in a like fashion. As used herein, the term "and\or" includes any and all combinations of one or more of the associated listed terms.

Some embodiments will now be described with reference to the figures. Like elements in the various figures will be referenced with like numbers for consistency. In the following description, numerous details are set forth to provide an understanding of various embodiments and/or features. It will be understood, however, by those skilled in the art, that some embodiments may be practiced without many of these details, and that numerous variations or modifications from the described embodiments are possible. As used herein, the terms "above" and "below", "up" and "down", "upper" and "lower", "upwardly" and "downwardly", and other like terms indicating relative positions above or below a given point are used in this description to more clearly describe certain embodiments.

Aspects of the disclosure relate to a portable rheology analyzer that is used in conjunction with hydrocarbon recovery operations. A sample hydrocarbon recovery operation will be described with reference to FIG. 1, along with the need for viscosity measurements performed by a portable rheology analyzer. As will be understood, rheological measurements may be made of drilling fluid at various points in the drilling operation. The drilling operation, therefore, will be discussed and possible fluid testing points will be discussed. The portable rheology analyzer may include a viscometer. Aspects of the disclosure relate to portions of the viscometer and provide components that provide for enhanced operations compared with conventional apparatus.

Figure 1:
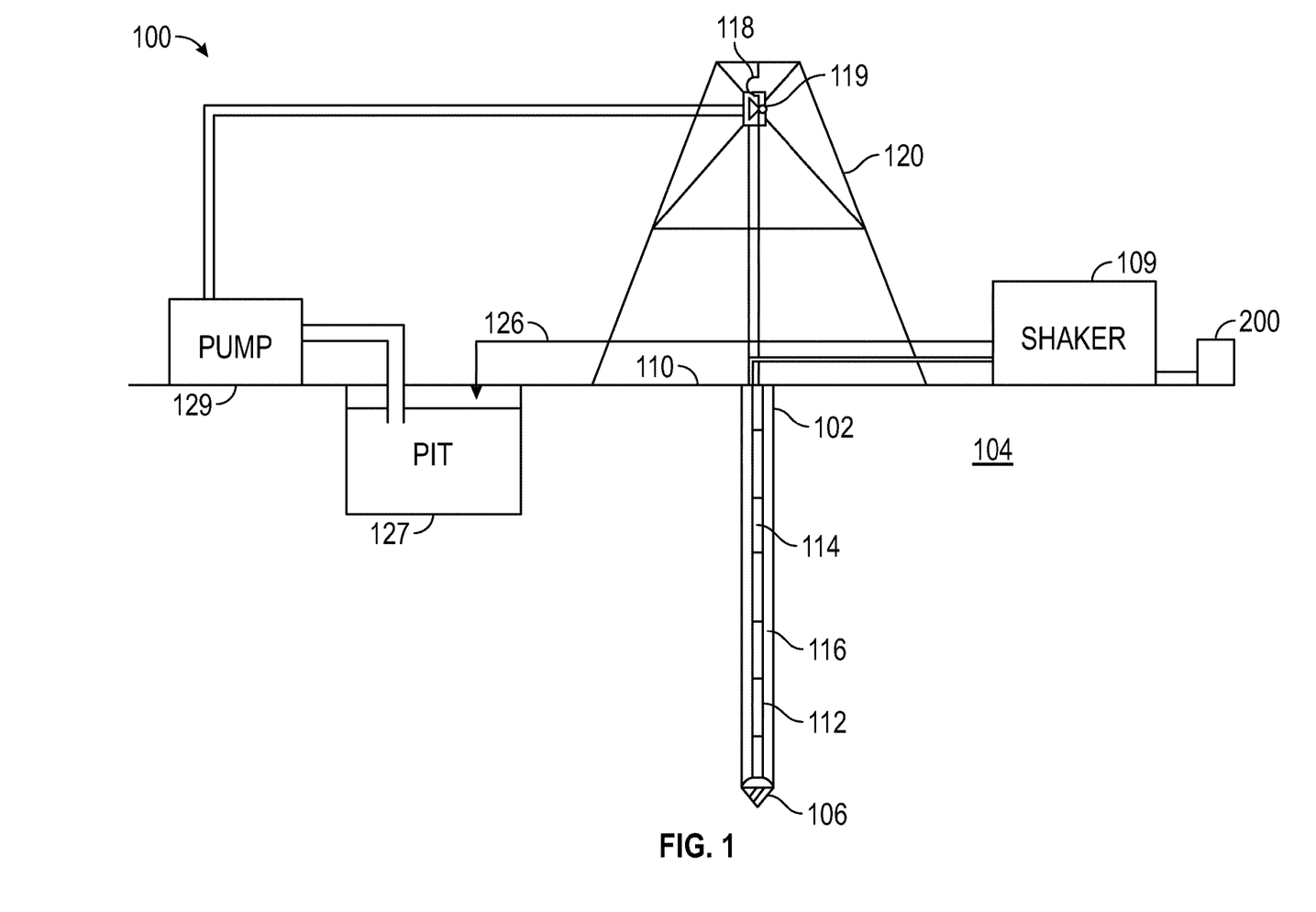
FIG. 1 is a drilling rig in which embodiments of the disclosure may be used.

Referring to FIG. 1, a drilling rig 100 is illustrated. The purpose of the drilling rig 100 is to recover hydrocarbons located beneath the surface 110. Different stratum 104 may be encountered during the creation of a wellbore 102. In FIG. 1, a single stratum 104 layer is provided. As will be understood, multiple layers of stratum 104 may be encountered. In an embodiment, the stratum 104 may be horizontal layers. In another embodiment, the stratum 104 may be vertical layers. In another embodiment, the stratum 104 may have both horizontal and vertical layers. Stratum 104 beneath the surface 110 may be varied in composition and may include sand, clay, silt, rock and/or combinations of these. Therefore, operators need to assess the composition of the stratum 104 in order to achieve a maximum penetration of a drill bit 106 that will be used in the drilling process. The wellbore 102 is formed within the stratum 104 by the drill bit 106. In an embodiment, the drill bit 106 is rotated such that contact between the drill bit 106 and the stratum 104 causes portions ("cuttings") of the stratum 104 to be loosened at the bottom of the wellbore 102. Differing types of drill bits 106 may be used to penetrate different types of stratum 104. Therefore, the type of stratum 104 encountered is an important characteristic for operators. The types of drill bits 106 may vary widely. In an embodiment, polycrystalline diamond compact ("PDC") drill bits may be used. In another embodiment, roller cone drill bits, diamond impregnated drill bits or hammer drill bits may be used. In an embodiment, during the drilling process, vibration may be placed upon the drill bit 106 to aid in the breaking of the stratum 104 that are encountered by the drill bit 106. Such vibration may increase the overall rate of penetration ("ROP"), increasing the efficiency of the drilling operations.

As the wellbore 102 penetrates further into the stratum 104, operators may add portions of drill string pipe 114 to form a drill string 112. As illustrated in FIG. 1, the drill string 112 may extend into the stratum 104 in a vertical orientation. In another embodiment, the drill string 112 and the wellbore 102 may deviate from a vertical orientation. In another embodiment, the wellbore 102 may be drilled in certain sections in a horizontal direction and parallel with the surface 110.

The drill bit 106 is larger in diameter than the drill string 112 such that when the drill bit 106 produces the hole for the wellbore 102, an annular space is created between the drill string 112 and the inside face of the wellbore 102. This annular space provides a pathway for removal of cuttings from the wellbore 102. Drilling fluids include water and specialty chemicals to aid in the formation of the wellbore 102. In an embodiment, the chemicals may be water-based chemicals. In another embodiment, the chemicals may be oil-based chemicals. Other additives, such as defoamers, corrosion inhibitors, alkalinity control, bactericides, emulsifiers, wetting agents, filtration reducers, flocculants, foaming agents, lubricants, pipe-freeing agents, scale inhibitors, scavengers, surfactants, temperature stabilizers, scale inhibitors, thinners, dispersants, tracers, viscosifiers and wetting agents may be added.

The drilling fluids may be stored in a pit 127 located at the drill site. The pit 127 may have a liner to prevent the drilling fluids from entering surface groundwater and/or contacting surface soils. In an embodiment, the drilling fluids may be stored in a tank alleviating the need for a pit 127. The pit 127 may have a recirculation line 126 that connects the pit 127 to a shaker 109 that may be configured to process the drilling fluid after returning from the downhole environment.

Drilling fluid from the pit 127 is pumped by a mud pump 129 that is connected to a swivel 119. The drill string 112 is suspended by a drive 118 from a derrick 120. In the illustrated embodiment, the drive 118 may be a unit that sits atop the drill string 112 and is known in the industry as a "top drive". The top drive may be configured to provide the rotational motion of the drill string 112 and the attached drill bit 106. Although the drill string 112 is illustrated as being rotated by a top drive, other configurations are possible. A rotary drive located at or near the surface 110 may be used by operators to provide the rotational force. Power for the rotary drive or the top drive may be provided by diesel generators.

Drilling fluid is provided to the drill string 112 through the swivel 119 suspended by the derrick 120. The drilling fluid exits the drill string 112 at the drill bit 106 and has several functions in the drilling process. The drilling fluid is used to cool the drill bit 106 and remove the cuttings generated by the drill bit 106. The drilling fluid with the loosened cuttings enter the annular area outside of the drill string 112 and travel up the wellbore 102 to the shaker 109.

The shaker 109 is configured to separate the cuttings from the drilling fluid. The cuttings, after separation, may be analyzed by operators to determine if the stratum 104 currently being penetrated has hydrocarbons stored within the stratum level that is currently being penetrated by the drill bit 106. The drilling fluid may then be recirculated to the pit 127 through the recirculation line 126. The shaker 109 separates the cuttings from the drilling fluid by providing an acceleration of the fluid on to a screening surface. As will be understood, the shaker 109 may provide a linear or cylindrical acceleration for the materials being processed through the shaker 109. In an embodiment, the shaker 109 may be configured with one running speed. In another embodiment, the shaker 109 may be configured with multiple operating speeds. The shaker 109 may be configured with a low speed setting of 6.5 "g" and a high-speed setting of 7.5 "g", where "g" is defined as the acceleration of gravity. Large cuttings are trapped on the screens, while the drilling fluid passes through the screens and is captured for reuse. Tests may be taken of the drilling fluid after passing through the shaker 109 to determine if the drilling fluid is adequate to reuse. Viscometers may be used to perform such testing.

As will be understood, smaller cuttings may pass entirely through the screens of the shaker 109 such that the fluids may include many smaller size cuttings. Therefore, the overall quality of the drilling fluid may be compromised by such smaller cuttings. It is then desired to test the drilling fluid through a portable rheology unit 200. Testing of the drilling fluid may occur after passing the drilling fluid through the screens of the shaker 109. Although illustrated as being positioned after the shaker 109, the portable rheology unit 200 may be used in other locations of the drilling rig. In an embodiment, multiple portable rheology units 200 may be used and located at different locations of the drilling rig. As the portable rheology unit 200 is portable, the portable rheology unit 200 may be repositioned to different places on the drilling rig 100 for measurement. As measurements are made at specific temperatures, operators may provide a temperature-controlled environment for the testing activities to be performed within. In the illustrated embodiment provided in FIG. 1, a single testing area is provided that is temperature controlled. Samples may be taken from different sections of the flow path for the drilling fluids, such as after the shaker 109 or from the pit 127 or a sample taken off the pump 129.

Figure 3:
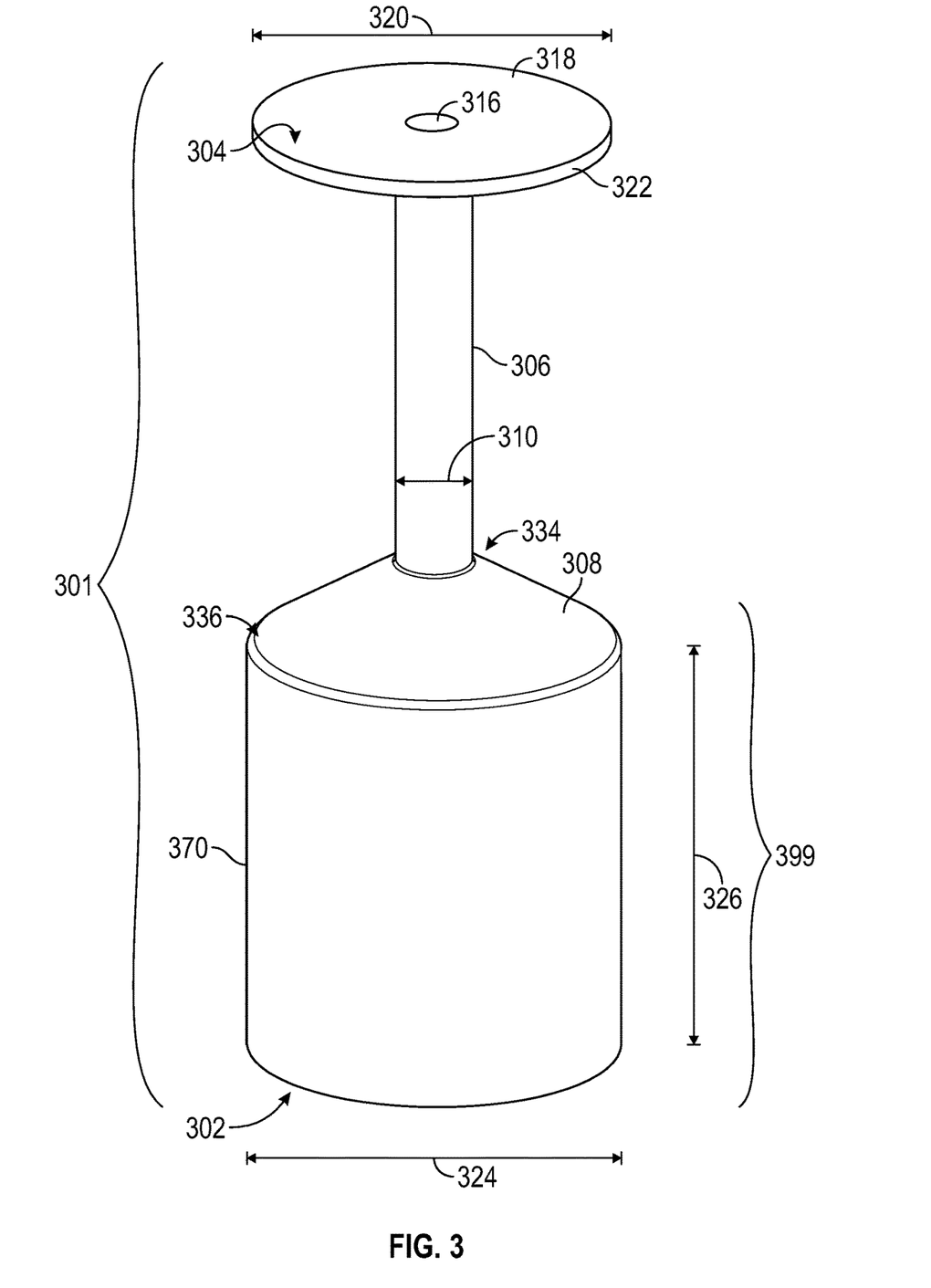
FIG. 3 is a side view of a bob and a sleeve portion of the viscometer of FIG. 2.
Figure 4:
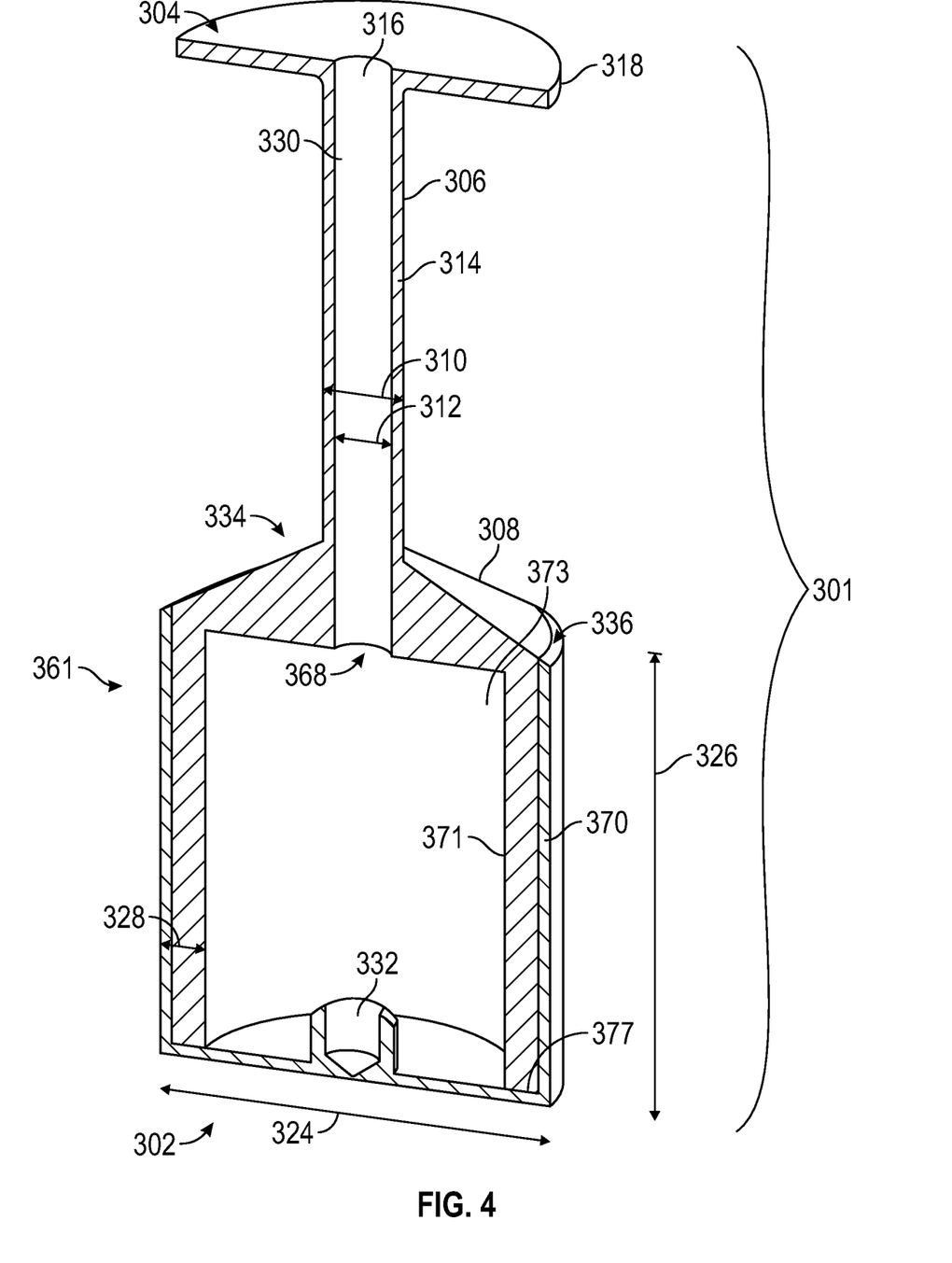
FIG. 4 is a cross-sectional view of the bob and sleeve portion of the viscometer of FIG. 3.

A portable rheology unit 200 may provide the capability of measuring rheological properties of different drilling fluids in the recovery of hydrocarbons. In an embodiment, a portable rheology unit 200 is described that will measure parameters, such as viscosity, of the drilling fluids used in recovery efforts. The portable rheology unit 200 may be operated at different speeds according to the drilling fluids analyzed. As portable rheology units 200 measure fluid properties to very exact values, deviations from calibrated values should be kept to a minimum. A sample portable rheology unit 200 that measures viscosity is described below and addresses the defects in conventional rheology units. As will be understood, the portable rheology unit 200 may have different components to measure different fluid properties. In an embodiment, the portable rheology unit 200 has a viscometer that has a bob 301 (FIGS. 2-4) and a sleeve 306 (FIGS. 3-4) construction. The bob 301 and the sleeve 306 construction are illustrated in FIGS. 3 and 4. The bob 301 and the sleeve 306 construction provide for insulation of drilling fluids being tested, different than conventional rheology unit construction, thereby providing a quicker sampling rate. Aspects of the present disclosure also utilize less energy to bring fluids up to testing temperature and are also more efficient than conventional rheology units.

Conventional portable rheology units are typically disassembled prior to shipping from a first location to a second location as a number of internal rotational components may degrade from forces exerted by shipping. As an example, conventional portable rheology units may spin a fluid at a relatively slow speed of 3 revolutions per minute ("rpm"). In other embodiments, different motor and drive combinations may provide slower speeds for measurement. In some embodiments, a variable speed motor with belt drive may be used to achieve different rotational speeds. In multi-speed units, however, rotational speeds may exceed 600 rpm. Therefore, the conventional portable rheology units generally have to be able to adapt to slow and fast speed operation. To accomplish this task, high quality bearings are used along the rotational axis of spin created by the conventional portable rheology unit. Bearings used in these conventional portable rheology units generally are not able to withstand lateral forces exerted during shipment of the rheology unit to a well site. Aspects of the disclosure solve these shortcomings by providing a durable portable rheology unit 200 that prevents stresses that damage the bearings during shipment. The bob 301 and the sleeve 306 portions of the viscometer of the portable rheology unit 200 are more economical to construct as the bob 301 and the sleeve 306 portions may be configured during an additive manufacturing process, such as a three-dimensional printer.

Figure 2:
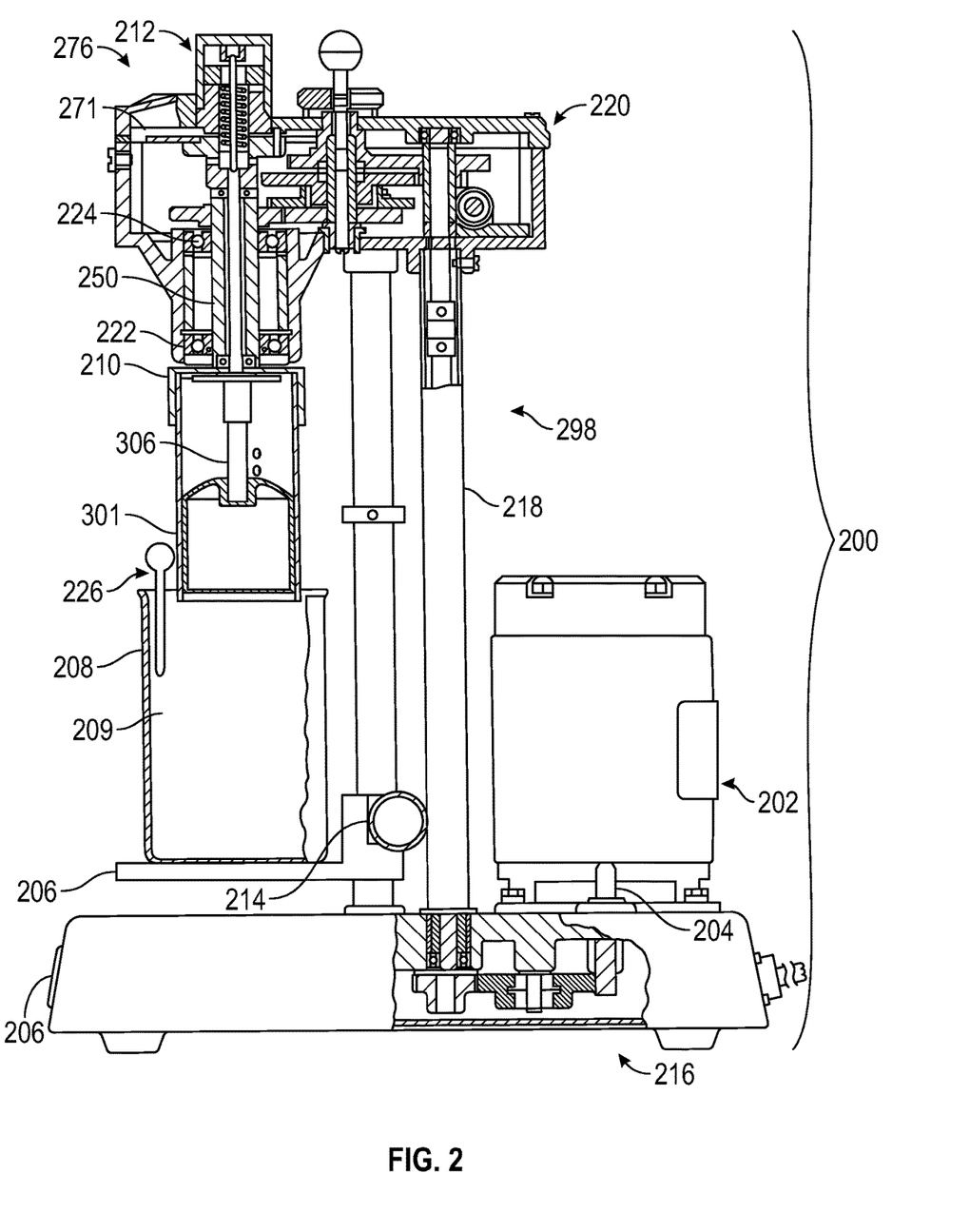
FIG. 2 is a cross-sectional view of a viscometer used in conjunction with the drilling rig of FIG. 1.

Referring to FIG. 2, an embodiment of a viscometer for a portable rheology unit 200 is illustrated. In this embodiment, a cup 208 with an interior 209 may be provided to contain drilling fluids added by an operator. The addition of the drilling fluids to the cup 208 may be automatically performed to limit the operational steps performed by the operator. In another embodiment, the operator may take a representative sample of drilling fluid being processed through the system and add these fluids to the cup 208. As discussed above, the sample may be taken from the pit 127 or directly after the shaker 109. In conventional portable rheology units, the drilling fluid is generally heated to a specific temperature prior to taking any viscosity readings. The increase of the temperature may take several minutes in order to obtain a desired temperature. Operators waiting for the sample to heat or cool limits the overall effectiveness of the conventional viscometers as a limited number of samples may be taken by operators. Aspects of the current disclosure, however, solve these issues in that heat loss from stainless steel components, a heat conductor, are minimized, which allows an operator to perform successive measurements quickly and accurately. Aspects of the disclosure provide an insulative material, such as a plastic, to prevent heat transfer and allow measurements to be made quickly as the fluid achieves a desired temperature more quickly than conventional portable rheology units and can maintain a desired temperature with less heat input from an external heating source. In other embodiments, a cooling unit may be used to cool temperatures of the fluid that are above the desired temperature for measurement.

The purpose of the viscometer of the portable rheology unit 200 is to determine a viscosity of fluid placed within the cup 208 that defines the interior 209. Fluid is poured into the cup 208, in this instance, drilling fluid. The cup 208 may be supported by a vertically movable platform 206. A lock knob 214 may be provided to allow a clamp mechanism to tighten, fixing the cup 208 to a desired vertical position. In an embodiment, a user may pour drilling fluid into the cup 208 when the cup 208 is in a low vertical position. In another embodiment, the cup 208 may have a fill line to illustrate the maximum amount of fluid that may be poured into cup 208. In an embodiment, the maximum amount of fluid that may be poured into the cup 208 may be 350 milliliters. In other embodiments, more or less amounts of fluid may be used. The platform 206 may be lifted such that both the platform 206 and the cup 208 resting upon the platform 206 are elevated, wherein a bob 301 enters the cup 208 and the drilling fluid. An electric motor 202 may be provided to provide rotational acceleration to the bob 301. The rotation acceleration is accomplished through a driving mechanism 298. In the illustrated embodiment, the driving mechanism 298 may be a first gearing 216, a first shaft 218 and a second gearing 220. In alternative embodiments, the driving mechanism may be a drive belt that connects the motor 202 to the bob 301.

In the illustrated embodiment, the second gearing 220 may be configured to allow the user to selectively increase or decrease the amount of rotation of the bob 301. In an embodiment, the second gearing 220 creates a resistance to the rotation created by the first gearing 216, the first shaft 218 and the motor 202. In another embodiment, the motor 202 may be provided with a rheostat that increases or decreases electricity to the motor 202 to be able to select speeds for the bob 301. The second gearing 220 may be connected to a second shaft 250 that is connected to the bob 301. The second shaft 250 may be configured to rotate upon rotation of the second gearing 220. The second shaft 250 rotation also rotates the connected bob 301.

Through the configuration illustrated for the viscometer of the portable rheology unit 200, the bob 301 may be configured to rotate within the cup 208 that has the drilling fluid. In an embodiment, the motor 202 may be an electric motor that is activated and deactivated through a switch 204. The switch 204 may be coupled to the motor 202 to run at different speeds, such as a low speed or a high speed. In an embodiment, the motor 202 may be configured to run and produce 300 rpm of the bob 301 within the cup 208. In another embodiment, the motor 202 may be configured to run and produce 600 rpm of the bob 301 within the cup 208.

The motor 202 may be configured to run at slow rotational speeds of the bob 301 within the cup 208. A user may vary the speed through the use of the switch 204 located near the motor 202 as well as a gear selector at the top of the viscometer of the portable rheology unit 200. In an embodiment, the switch 204 may be configured with a high-speed selection that is separate from a low-speed selection. Another selection for the switch 204 may also be configured to stop the motor 202.

The rotational acceleration provided by the motor 202 to the drilling fluid within the cup 208 will cause centripetal acceleration of the drilling fluid. A sleeve 306, illustrated in FIG. 3, may be kept in place by a first bearing system 222 and a second bearing system 224. In conventional portable rheology units, the bearing arrangements have significant force exerted upon them during any lateral motion that the viscometer encounters. During shipping, for example, a conventional bob has a significant weight near an end of the bob. This weight, when accelerated laterally, will cause a sheer and a moment to be exerted at each bearing system down the entire shaft. As bearings are typically poor at resisting such forces, the bearing systems become dislodged or move. A smooth rotational operation of the bob 301, therefore, is not permitted. In the illustrated embodiment, however, the light-weight construction of the bob 301 allows for transportation of the viscometer of the portable rheology unit 200 with the bob 301 and the sleeve 306 installed.

In an embodiment, two separate bearing arrangements may be provided, namely a first bearing system 222 and a second bearing system 224. Both the first bearing system 222 and the second bearing system 224 may be a cylindrical roller bearing. Other configurations of bearings may also be used for the first bearing system 222 and the second bearing system 224, such as a spherical ball bearings, ball screw support bearings, or tapered bearings. Additional bearing systems may be used in the construction of the viscometer of the portable rheology unit 200. In an embodiment, a bearing system may be used near a first end 302 (FIG. 3) of the bob 301. Such a configuration may allow for prevention of wobble during rotation speeds that are at the upper rotational speed ranges of the viscometer of the portable rheology unit 200. In some embodiments, a speed limiter may be used to prevent excessive speeds from being used during the measurement process.

A torsion measuring apparatus 276 is provided Results from the torsion measuring apparatus 276 may be read on a display 271. The torsion measuring apparatus 276 may be a torsion spring 212. In embodiments utilizing a torsion spring 212, the torsion spring 212 is connected to the bob 301 such that resistance exerted by the fluid on the bob 301 during rotation will cause a deflection of the torsion spring 212. In other embodiments, the torsion spring 212 may be replaced by a strain gauge connected to the display 271. In some embodiments, a dial gauge is used as the display 271 when a torsion spring 212 is used. As will be understood, a greater resistive force on the bob 301 during rotation from the motor 202 will cause a greater spring deflection of the torsion spring 212 and a higher reading upon the dial gauge. In another embodiment, the gauge may be a digital gauge. The readings from the dial gauge may be provided to the reader directly from the viscometer section of the portable rheology unit 200, or the data may be provided to the portable rheology unit 200 for display to a user.

In an embodiment, a computing system may be provided with either the portable rheology unit 200 or the viscometer. The computing system may be configured to store data as measured by the viscometer. The computing system may be provided with a non-volatile memory system that will store data when electricity is removed from the computing system. In another embodiment, the non-volatile memory system may be a hard disk storage unit, a flash drive memory unit or a solid-state hard drive. The computing system may also be configured with an output that will allow a user to connect a portable device, such as a universal serial bus ("USB") drive to download data from the computing system for transportation and use by operators. The computing system may be, for example, a personal computer equipped with software to store data generated with samples. In another embodiment, an application specific integrated circuit "ASIC" may be provided for computing and storage operations. Output for the computing system may be visually through a video screen. In another embodiment, output of the computing system may be through a printer.

In an embodiment, a temperature gauge or thermometer 226 may be provided. In some fluids the fluids may have different properties under different temperatures. To ensure the drilling fluid is tested at a necessary temperature, the thermometer 226 is used for verification. Although not shown for clarity of detail, a heater and/or cooler may also be included for the cup 208 so that a specific temperature is maintained throughout the testing of the drilling fluid. In other embodiments, a cooling arrangement may be provided for cooling of the fluid. The heater may be an electric heater, such as an electrical resistance coil unit. The heater may also be configured with a calibrated heat input temperature system that interfaces with the thermometer 226. In another embodiment, when a desired input temperature has been achieved, as measured by the thermometer 226, heat input may be reduced to prevent over-heating of the fluid sample within the cup 208. In embodiments, the motor 202 may be a variable speed motor that drives the bob 301 through a belt drive. In this embodiment, the motor 202 is configured to be operated through a control system that allows for precise control of motor 202 speed for rotation of the bob 301.

Referring to FIG. 3, a side view of the bob 301 is illustrated. In this view, the bob 301 has been removed from the viscometer of the portable rheology unit 200 for clarity of illustration. It will be understood, however, that the purpose of the design of the bob 301 and the sleeve 306 is to allow for the bob 301 and the sleeve 306 to remain within the viscometer of the portable rheology unit 200 during shipping. The aspects of the disclosure allow the bob 301 to remain within the viscometer of the portable rheology unit 200 preventing damage to either the first bearing system 222 or the second bearing system 224. The bob 301, contrary to conventional designs, provides a very compact and light weight to minimize structural forces on any of the bearing arrangements 222, 224. The bob 301 has a bob portion 399 that has a bob depth 326 and a first end diameter 324. The bob portion 399 has a cup shape with a first end portion 377 (FIG. 4) that defines the first end 302 of the bob 301 and an exterior portion 370 covering the exterior of the first end portion 377. The bob 301 may be configured with a cylindrical portion 361. The outside surface of the cylinder, in an embodiment, may be configured from a stainless steel that has a bob thickness 328 (FIG. 4). Inside the bob 301, as described in conjunction with FIG. 4, the bob 301 has a hollow plastic cylindrical core. The stainless steel exterior provides a non-corrosive wear surface when the bob 301 is rotated in the cup 208, as described in FIG. 2. The bob depth 326 may be configured such that a fill line for the cup 208 is below the value of the bob depth 326 such that fluid does not flow over the bob depth 326 onto a conical area 308 of the bob 301. As illustrated, the conical area 308 may be configured from a lightweight plastic. Example embodiments of plastics that may be used for the construction of the bob 301 and the sleeve 306 may include, but are not limited to, polyethylene terephthalate (PET), high-density polyethylene (HDPE), Polyvinyl chloride (PVC), low density polyethylene (LDPE) and polypropylene (PP).

The conical area 308 extends from a conical area first end 334 to a conical area second end 336. In an embodiment, the conical area 308 may be configured with a void section 368 that matches an internal sleeve diameter 312. According to a first end diameter 324, the conical area 308 extends from the conical area first end 334 to the conical area second end 336. In another embodiment, the angle of extension from the conical area second end 336 to the conical area first end 334 may be approximately 20 degrees. In another embodiment, the amount of angle of extension may be greater or lesser than 20 degrees.

In an embodiment, the conical area 308 from the conical area first end 334 to the conical area second end 336 may be made of a solid construction of plastic. Such a configuration allows for a rigid construction between the sleeve 306 and the bob 301. Other configurations are possible wherein the conical area 308 may be a void to allow for a lighter weight construction.

A sleeve 306 extends from the conical area first end 334 to a second end portion 304 of the bob 301. In an embodiment, the second end portion 304 may be configured in a shape of a disk 318 with a disk thickness 322. The second end portion 304 may also be configured with a disk diameter 320. A port 316 may be provided in the center of the disk 318. The port 316 allows access to an interior of the sleeve 306 and the bob 301. The port 316 allows for making a hollow interior of the sleeve 306, thereby reducing the weight of the sleeve 306 and the bob 301.

The sleeve 306 may have a hollow interior and a light weight construction. If more structural rigidity is necessary, the sleeve 306 may be configured with sturdier plastic material to reduce any possible bending of the sleeve 306. Structural supports placed within the sleeve 306 may be lattice bracing. In an embodiment, the lattice bracing may be positioned such that the sleeve 306 is evenly braced and that rotation of the sleeve 306 does not cause an imbalance when the sleeve 306 and the bob 301 are rotated. In another embodiment, the sleeve 306 construction may be made through additive manufacturing techniques, as described below.

The bob 301 and the sleeve 306, with the exception of the exterior surface of the bob 301 that is configured to be stainless steel, may be made of plastic. Different methods of forming plastic may be used to form the bob 301 and the sleeve 306. In an embodiment, the methods that may be used include, but are not limited to, compression molding, thermoforming, vacuum casting, reaction injection molding, injection blow molding, extrusion blow molding, rotational molding, plastic injection molding and additive manufacturing. Types of additive manufacturing that may be used include powder bed fusion, vat photopolymerization, binder jetting, material extrusion and directed energy deposition. Although illustrated as having a single type of plastic used throughout the bob 301 and the sleeve 306, layers of different plastic may be used in the construction of the bob 301 and the sleeve 306. As an example, a first plastic layer may be used for structural loading capabilities that the bob 301 and the sleeve 306 may be exposed to during service operations, while a second plastic layer may be used for insulation purposes to allow drilling fluids to achieve desired temperatures quicker than conventional apparatus.

The exterior surface of the bob portion 399 may be made from stainless steel. In the formation of the cylinder from stainless steel, different types of stainless steel cutting may be used if the cylinder is constructed from an ingot of stainless steel. Cutting methods may be, as an example, plasma cutting, laser cutting, water jet cutting, band sawing, slitting and abrasive disk cutting. The stainless steel used may contain a minimum of 10.5% chromium content by mass and a maximum of 1.2% carbon by mass. Some embodiments of stainless steel materials may be ASTM 304, ASTM 316, AST 2205 and ASTM 2304, where ASTM is the American Society of Testing Materials.

A connection between the stainless steel exterior portion 370 of the bob 301 and a plastic interior portion 371 (FIG. 4) may be established such that the two sections 370, 371 are joined. The joining of these two portions 370, 371 may be through various connection technologies. In an embodiment, the exterior portion 370 of the bob 301 and the interior portion 371 are connected through an adhesive. The adhesive may be a polyamide epoxy, a polyamine epoxy, a phenolic epoxy, or a novolac epoxy. In another embodiment, a mechanical connection may be established between the exterior portion 370 and the interior portion 371. The mechanical connection may be through a screw connection. In the instance of a mechanical connection established between the exterior portion 370 and the interior portion 371, the screw direction may be opposite of the direction of motion during operation, minimizing the possibility of the mechanical connection unscrewing during operation of the bob 301.

Referring to FIG. 4, a cross-section of the bob 301 and sleeve 306 configuration is illustrated. In FIG. 4, the bob 301 extends from the first end 302 to the second end portion 304. At the first end 302 of the bob 301, a cylinder 332 is positioned within the open volume 373. The open volume 373 is defined, at least in part, by an inner surface of the plastic interior portion 371 (e.g. the surface defining the bore of the plastic interior portion) and the first end portion 377. In an embodiment, a rod, not shown for illustrative clarity, may penetrate the cylinder 332 at the first end 302 of the bob 301 and extend upward through the hollow sleeve 306 and penetrate the port 316 up to the second gearing 220 (FIG. 2). A connection between the rod and the bob 301 or the sleeve 306 may be established such that rotation of the rod rotates the bob 301 and the sleeve 306. In another embodiment, the connection between the rod and cylinder 332 is through a keyway. In this embodiment, the key may be located on the rod, and the bob 301 may be configured with the keyway. To prevent stripping of the keyway within the cylinder 332, the cylinder 332 may have a reinforced area to prevent shear forces.

The sleeve 306 may be configured with a sleeve thickness 314. The sleeve 306 may be configured with an internal sleeve diameter 312. The internal sleeve diameter 312 may be sized to fit an external diameter of the rod penetrating the bob 301. The bob 301 may have a bob thickness 328 that includes the stainless steel exterior portion 370 and a plastic thickness interior portion 371. In an embodiment, the hollow portion of the bob 301 and the sleeve 306 extend through the second end 304. The sleeve 306 may be configured with a constant diameter internal sleeve diameter 312. In another embodiment, the sleeve 306 may be provided with a tapered diameter or another type of varying diameter configuration.

The first end 302 may be constructed from stainless steel. In another embodiment, the first end 302 may be constructed from plastic. In another embodiment, the first end 302 may be constructed from both an exterior portion of stainless steel and an interior portion of plastic. In an embodiment, the cylinder 332 provides a seat for the rod, not illustrated. The cylinder 332 may be made from stainless steel. As will be understood, in the embodiments disclosed wherein stainless steel may be used, such as in exterior portions of the bob 301, other metallic materials may be used such as aluminum or other non-reactive metals. In another embodiment, the bob 301 may be used at higher temperatures than conventional apparatus wherein area 373 is not connected through port 316. The internal sleeve diameter 312, in this embodiment may have a smaller diameter than shown in FIG. 4.

Figure 5:
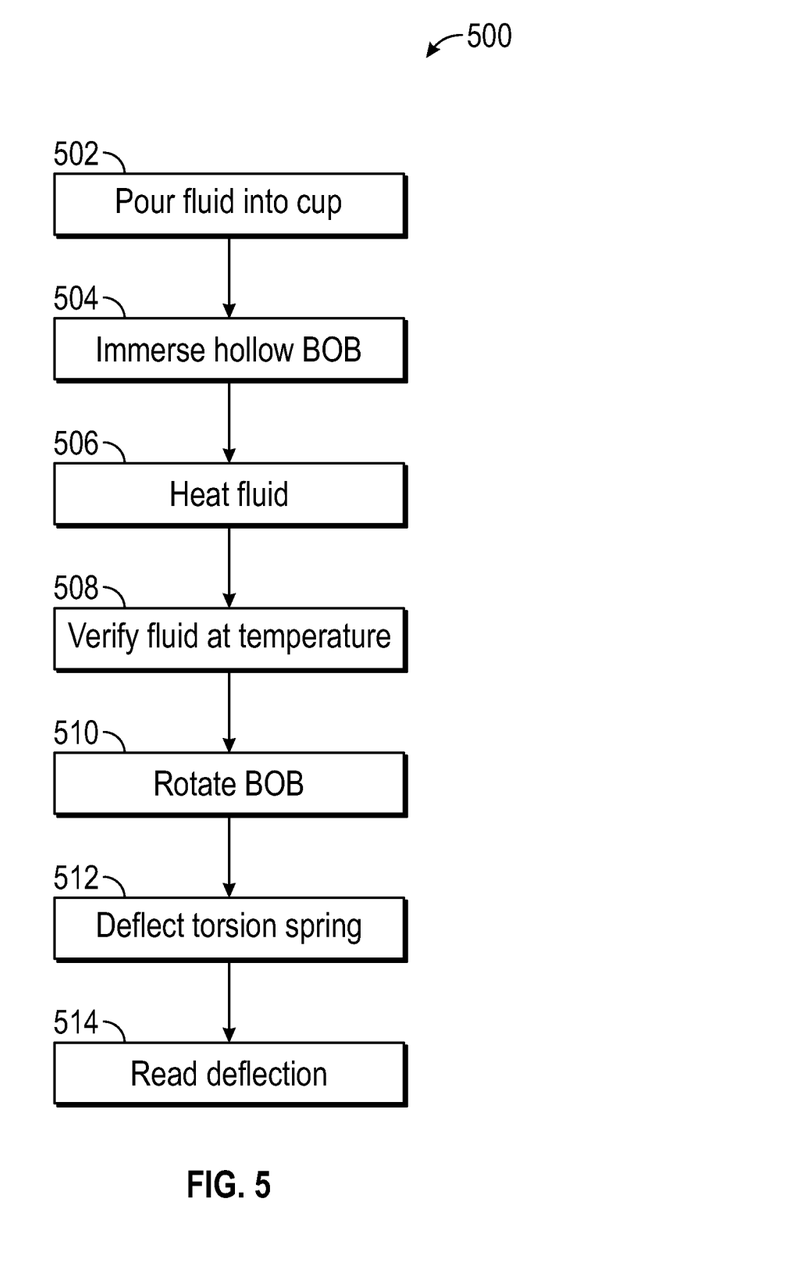
FIG. 5 is a method to take a viscosity measurement of a drilling fluid with a bob and sleeve design as illustrated in FIGS. 3 and 4.

Referring to FIG. 5, a method 500 of performing a viscosity test of drilling fluid is illustrated. At 502, the method may include pouring a drilling fluid into a sample cup of a viscometer. The viscometer may be a component of a portable rheology unit. In embodiments, the provision of drilling fluid may be automatic by a fluid delivery system. At 504, the method may further include immersing a hollow bob with an attached hollow sleeve into the drilling fluid poured into the sample cup. At 506, the method may also include heating and/or cooling the drilling fluid with a heater to a desired testing temperature. At 508, the method may further include verifying the drilling fluid is at the desired testing temperature with a thermometer. At 510, after the drilling fluid has been verified to be at the desired testing temperature, the hollow bob is rotated within the drilling fluid. At 512, the method further comprises deflecting a torsion spring from viscous drag forces created between the hollow bob and the drilling fluid. At 514, the method further comprises interpreting an amount of defection from the torsion spring. The interpretation of the amount of deflection of the torsion spring may occur through visual observation of a dial or may be through a sensor connected to the computing system that has been calibrated to accept and save data related to the interpretation.

The foregoing description of the embodiments has been provided for purposes of illustration and description. It is not intended to be exhaustive or to limit the disclosure. Individual elements or features of a particular embodiment are generally not limited to that particular embodiment, but, where applicable, are interchangeable and can be used in a selected embodiment, even if not specifically shown or described. The same may be varied in many ways. Such variations are not to be regarded as a departure from the disclosure, and all such modifications are intended to be included within the scope of the disclosure.

While embodiments have been described herein, those skilled in the art, having benefit of this disclosure, will appreciate that other embodiments are envisioned that do not depart from the inventive scope. Accordingly, the scope of the present claims or any subsequent claims shall not be unduly limited by the description of the embodiments described herein.

What is claimed is:

1. A bob for a viscometer in a portable rheology unit, comprising:

an exterior portion comprising a cylindrical portion and a first end portion, wherein the first end portion defines a first end of the bob;

a plastic interior portion comprising a first interior portion end, a conical area, and a bore, the first interior portion end interfacing with an interior surface of the first end portion, the conical area extending from a conical area first end to a conical area second end, the conical area second end being connected to an interior surface of the cylindrical portion, and the bore defined by an interior surface of the plastic interior portion; and a sleeve portion connected to the plastic interior portion, the sleeve portion extending from the conical area to a second end of the bob.

2. The bob of claim 1, wherein the second end is configured in a disk shape.

3. The bob of claim 2, wherein the second end defines a port.

4. The bob of claim 3, wherein the sleeve portion is hollow and is connected to the port.

5. The bob of claim 1, wherein the conical area defines a void section connected to the sleeve portion.

6. The bob of claim 5, wherein the void section has a diameter equal to a hollow diameter of the sleeve portion.

7. The bob of claim 1, wherein the sleeve portion and the second end are made of plastic.

8. A viscometer in a portable rheology unit, comprising:
a motor;
a switch operatively connected to the motor, wherein the switch is configured to connect the motor to an electrical source;
a cup with an interior configured to hold a drilling fluid;
a bob configured to be at least partially submerged in the fluid, the bob comprising:
an exterior portion comprising a cylindrical portion and a first end, wherein the first end defines a first end of the bob;
a plastic interior portion comprising a first interior portion end, a conical area, and a bore, the first interior portion end interfacing with an interior surface of the first end, the conical area extending from a conical area first end to a conical area second end, the conical area second end being connected to an interior surface of the cylindrical portion, and the bore defined by an interior surface of the plastic interior portion; and
a sleeve portion connected to the plastic interior portion, the sleeve portion extending from the conical area to a second end of the bob;
a driving mechanism connected to the bob and the motor, wherein the driving mechanism conveys rotational movement from the motor to the bob to rotate the bob;
a strain gauge configured to measure a torsion resistance of fluid interacting on the exterior portion of the bob; and
a platform configured to support the cup, wherein the platform is configured to move from a first position wherein the bob is outside of an interior of the cup to a second position wherein at least a portion of the bob is located within the interior of the cup.

9. The viscometer of claim 8, wherein the motor is a variable speed motor.

10. The viscometer of claim 8, further comprising:
a first bearing system positioned around a second shaft coupled to the second end of the bob.

11. The viscometer of claim 10, further comprising:
a second bearing system positioned around the second shaft.

12. The viscometer of claim 10, further comprising:
a thermometer configured to read a temperature of the fluid within the cup.

13. The viscometer of claim 12, further comprising:
an electric heater configured to heat or cool the fluid within the cup.

14. A method of performing a viscosity test, comprising:
pouring a drilling fluid into a cup of a viscometer;
immersing a bob into the drilling fluid within the cup, the bob comprising:
an exterior portion comprising a cylindrical portion and a first end, wherein the first end defines a first end of the bob;
a plastic interior portion comprising a first interior portion end, a conical area, and a bore, the first interior portion end interfacing with an interior surface of the first end, the conical area extending from a conical area first end to a conical area second end, the conical area second end being connected to an interior surface of the cylindrical portion, and the bore defined by an interior surface of the plastic interior portion; and
a sleeve portion connected to the plastic interior portion, the sleeve portion extending from the conical area to a second end of the bob;
rotating the bob in the drilling fluid with a motor; and
reading a viscous drag of the drilling fluid on the bob by a torsion measuring apparatus.

15. The method according to claim 14, further comprising:
altering a temperature of the drilling fluid in the cup with a heater after the pouring of the drilling fluid into the cup to a specified temperature.

16. The method according to claim 15, further comprising:
taking a temperature of the drilling fluid after the altering the temperature to verify the specified temperature has been achieved.

17. The method according to claim 14, wherein the reading the viscous drag of the drilling fluid on the bob is through a gauge.

18. The method according to claim 14, wherein the reading the viscous drag of the drilling fluid on the bob is through a display.

* * * * *